United States Patent
Feins (10) Patent No.: US 7,655,639 B2
(45) Date of Patent: Feb. 2, 2010

(54) MINIMALLY INVASIVE CLINICAL TREATMENT METHOD FOR CLOSURE OF UMBILICAL HERNIAS

(75) Inventor: Neil R. Feins, Brookline, MA (US)

(73) Assignee: Chidren's Medical Center Corporation, Boston, MA (US)

( * ) Notice: Subject to any disclaimer, the term of this patent is extended or adjusted under 35 U.S.C. 154(b) by 351 days.

(21) Appl. No.: 11/386,882

(22) Filed: Mar. 22, 2006

(65) Prior Publication Data

US 2006/0247206 A1 Nov. 2, 2006

Related U.S. Application Data

(60) Provisional application No. 60/664,708, filed on Mar. 23, 2005.

(51) Int. Cl.
*A61K 31/721* (2006.01)
*A61K 31/728* (2006.01)
*C08B 37/02* (2006.01)
*C07H 5/04* (2006.01)
*C07H 5/06* (2006.01)

(52) U.S. Cl. ............ 514/54; 514/59; 536/55.1; 536/55.2; 536/112

(58) Field of Classification Search ............ None
See application file for complete search history.

(56) References Cited

U.S. PATENT DOCUMENTS

| 7,166,570 B2 * | 1/2007 | Hunter et al. ............ 514/2 |
| 2004/0092970 A1 * | 5/2004 | Xavier ............ 606/151 |

* cited by examiner

*Primary Examiner*—Shaojia Anna Jiang
*Assistant Examiner*—Eric S Olson
(74) *Attorney, Agent, or Firm*—Nixon Peabody LLP (57) ABSTRACT

The present invention is a minimally invasive clinical method for closing hernias and other abnormal openings existing within the body; and is a unique alternative to conventional surgery and routine surgical techniques for correcting such medical defects. The clinical applications for the present methodology can be used for the in-vivo closure of small sized lumens and voids which naturally occur and exist internally within the soft connective tissue and organs of the living human body; can be employed to advantage for the closure of hernias generally; and is focused upon the closure of umbilical hernias specifically.

8 Claims, 3 Drawing Sheets

MINIMALLY INVASIVE CLINICAL TREATMENT METHOD FOR CLOSURE OF UMBILICAL HERNIAS

PRIORITY CLAIM

The present invention was first filed on Mar. 23, 2005 as U.S. Provisional Patent Application Ser. No. 60/664,708. The priority and legal benefit of this first filing is expressly claimed.

FIELD OF THE INVENTION

The present invention is directed to medical procedures for the in-vivo closure of lumens and voids which naturally occur and exist within the soft connective tissues and organs of the living human body; and is focused upon methods for the closure of hernias generally, and of umbilical hernias in particular.

FIELD OF THE INVENTION

A. The Medical Perspective

By medical definition, a hernia is the protrusion of a loop or a segment of tissue through an abnormal opening or lumen which is found to exist within the surrounding normal tissues of the living body. A variety of diverse and distinct types of hernias are medically known and recognized. Some of these include diaphragmatic, epigastric, esophageal, hiatal, incarcerated, inguinal, peritoneal, retrosternal, Richter's, strangulated, and umbilical hernias. Each of these is anatomically unique and is viewed as a medically different problem.

As one example, an umbilical hernia is a protrusion of the peritoneum or a portion of the abdominal organs through a small hole or void space which is present in the abdominal wall around the navel of the human body. Typically, the defect appears as a soft swelling under the skin; is of varying size; contains the umbilical vessels present at birth; and normally self-constricts and is ablated during the first 2 years of life.

An umbilical hernia is caused by incomplete closure of the anatomic area where the umbilical cord was attached at birth. Such hernias are most common in infants and usually close naturally by the time the child is 5 years of age. In adults, such a hernia may indicate and is associated with increased abdominal pressure from masses, fluid, or obesity.

In children, an umbilical hernia is typically a hole varying from 1-5 cm in diameter; and invasive surgery was previously and remains to date the treatment procedure of choice. It will be noted also that large umbilical hernias (i.e., those abnormal opening greater than about 2.5 cm in diameter) must be surgically closed because defects of such spatial size are very unlikely to close naturally if left unattended. Furthermore, physicians are far more concerned about umbilical hernias occurring in females, because it is very desirable to be sure that the abnormal opening, regardless of its diameter size, is closed early in life (i.e., before puberty) in order to prevent the defect from opening again later in mature life during a pregnancy. In addition, some parents insist that the surgical operation for closure of the hernia be performed as a matter of reducing health risks at the earliest possible time in like for the child.

In short, invasive surgery is almost invariably the remedial procedure employed for correction of hernias in general, and for the effective closure of umbilical hernias in particular. Granted, the well recognized medical risks common to any type of invasive surgery exist for the patient; and the morbidity and mortality statistics for this kind of surgery are much the same as for other kinds of surgery. For these reasons, among others, effective alternatives to surgical correction as a treatment procedure have long been sought.

B. DEFLUX Polysaccharide Gel

In recent years, Q-Med AB (Sweden) has commercially manufactured and sold a polysaccharide gel composition under the trademark DEFLUX. This gel is a cross-linked composition comprised of two well known types of polysaccharides: dextranomer microspheres and hyaluronic acid. Both of these substances are tissue-friendly and biocompatible in-vivo; both are well characterized from earlier applications in medicine; and both constitute substances which are broken down and degraded slowly within the human body by natural metabolic processes.

The Gel Composition and its Unique Mechanism of Action

The process for making the DEFLUX gel composition is well described within and legally protected by U.S. Pat. No. 5,827,937 issued Oct. 27, 1998, the text of which is expressly incorporated by reference herein.

As advertised commercially, DEFLUX gel is intended to be used primarily for the endoscopic treatment of vesicouretic reflux of "VUR" [see for example, Stenberg, A. & G. Lackgren, *J. Urology* 154:800-803 (1995)]. Notably, the DEFLUX gel composition has received FDA approval for sale in the U.S. for the treatment of VUR grades II-IV; and its use was approved in June 2003 in Canada for identical medical treatment purposes.

As described in the published scientific literature, DEFLUX polysaccharide gel does not function in-vivo directly as a blocking or sealing agent. Neither is the cross-linked gel composition utilized as a solid filler matrix, nor is it employed as a hole plugging material. Instead, the empirically demonstrated in-vivo effect and consequence of introducing DEFLUX polysaccharide gel at a pre-chosen anatomic site is that the dextranomer microspheres in the gel induce a new ingrowth of fibroblasts at the site of the gel's introduction; and that the newly ingrown fibroblasts, as a secondary outcome and consequence, in turn generate newly formed collagen fibers in-situ around the dextranomer microspheres.

Clearly, there are no collagen or elastin fibers as such in any form (cross-linked or not cross-linked) within the originally prepared gel formulation itself; and, accordingly, there is a complete absence of any discrete fibers at all in the gel composition at the time of its intended use in-vivo. Thus, it is solely via the secondary and indirect effect in-vivo that a formation and aggregation of newly formed collagen and elastin fibers occurs in-situ; and whereby a discrete mass at the anatomic site of such newly generated fibers then serves to occlude and fill whatever opening(s) previously existed at that anatomic locale.

In this manner and via this indirect mode of activity, the DEFLUX gel composition acts only to induce fibroblast growth at the selected anatomic site, but does not itself provide or form the collagen/elastin subsequently found at that locale. This difference and distinction as to the in-vivo mode of action for DEFLUX polysaccharide gel appears to be unique.

Dissimilarities and Differences from Other Gel Products

The DEFLUX polysaccharide gel composition is remarkably markedly different from and is not substantively similar to any of the following:

(i) A biocompatible composition having physiologically stable microparticles which are a hard, metallic substance and are carbon-coated [see U.S. Pat. No. 5,451,406];

(ii) A composition comprising textured microparticles having an outside diameter between 30-3000 microns [see U.S. Pat. No. 5,258,028];

(iii) A bio-osmotic gel consisting substantially of a biocompatible organic polymer and a solution of biocompatible salt, and which exhibits osmotic qualities closely paralleling that of human body serum and improved radiolucency with respect to silicone oil and saline [see U.S. Pat. No. 5,067,965];

(iv) A self-expandable, restorable implant article which is delivered in a compressed configuration and self-expands to conform to the shape of a soft tissue void [see U.S. Pat. No. 5,571,181];

(v) A collagen preparation formed from a collagen selected from the group consisting of Type I Collagen, Type III collagen, and a mixture thereof into a particulate collagen having a particle size from about 1-50 microns [see U.S. Pat. No. 5,196,185];

(vi) A dense collagen membrane matrix material [see U.S. Pat. No. 5,206,028];

(vii) A collagen matrix formed of collagen fibrils that are not chemically cross-linked, have a bulk density of 0.01-0.3 $g/cm^3$, and a pore population in which at least 80 percent of the pores have an average pore size of 35-250 microns [see U.S. Pat. No. 5,110,604];

(viii) A composition comprising restorable collagen matrix beads having an average pore size of 50-350 microns and a collagen content from 1-30 percent by volume of the beads [see U.S. Pat. No. 4,837,285]; and (ix) A collagen material comprised of reconstituted, mechanically sheared atelopeptide collagen fibers [see U.S. Pat. No. 4,642,117].

C. Some Conventionally Known Medical Treatment Alternatives

It will be appreciated also that medical research investigators and clinicians routinely search for alternative treatment procedures which can be usefully employed in lieu of surgical operations for the repair, reconstruction, or reconditioning of living tissues. It is therefore deemed to be both appropriate and of value to identify merely some representative and illustrative examples of such alternative treatment products, use protocols, and treatment procedures. The following brief summary, which reviews and evidences the substance of these developments and alternative procedures, is provided for this purpose. The texts of the individual documents are also expressly incorporated by reference herein.

U.S. Pat. No. 5,827,937 (Hereinafter the '937 Patent)

The '937 patent describes the preparation of biocompatible polysaccharide gels which can incorporate and release a biologically active substance. The advantages of gels prepared by this process are said to include: polymerization can be continued and an activated polysaccharide obtained; the gel polysaccharide does not form a compact or dense structure; and an irreversible gel structure is generated which does not swell to any appreciable extent when placed in contact with water or any aqueous medium.

The range of biologically active substances which can be incorporated into the composition of the cross-linked polysaccharide gel is said to be limited only by the intended use of the substance in prior cases. In other words, the condition to be treated should be decisive for the specific substance to be selected for use. Representative of such gel preparations are gels using dextranomer particles; gels using heparin; gels using GMCSF, and gels using hyaluronic acid.

Among the intended medical uses and therapeutic purposes for these prepared polysaccharide gels are tissue augmentation and hormone treatment of a mammal, especially a human. A gel preparation suitable for tissue augmentation purposes would thus follow the recipe stated in PCT Publication No. WO/94/21299, and comprise a polymer selected from collagen, starch, dextranomer polysaccharide and copolymers thereof, a poly-β-hydroxibutyrate and copolymers thereof. For hormonal treatments, erythropoietin and calcitonin are especially preferred.

U.S. Pat. No. 6,432,437 (Hereinafter the '437 Patent)

The '437 patent discloses a biocompatible material for soft tissue augmentation and describes methods for its use. The biocompatible material comprises a matrix of smooth, rounded, substantially spherical, finely divided particles of ceramic matter, such as calcium hydroxyapatite. Other suitable ceramic matter includes calcium phosphate-based materials, alumina-based materials, and the like; and are exemplified tetracalicum phosphate, calcium pyrophosphate, tricalcium phosphate, octacalicum phosphate, calcium fluoroapatite, calcium carbonate apatite, and combinations thereof.

The '437 patent describes the process of preparing finely divided augmentation material in substantive detail. The range of permitted particle sizes and the extent of particle size distributions is disclosed at length.

The prepared ceramic material matrix can be homogeneously suspended in a lubricous gel for delivery to the tissue site where augmentation is desired; and this procedure will provide a scaffold or lattice for autogenous, three-dimensional, randomly oriented, non-scar tissue growth at the chosen augmentation site. The augmentation material is said to be especially suitable for urethral sphincter augmentation; for the treatment of incontinence; for filing soft tissue voids; for creating soft tissue blebs; for the treatment of vocal cord paralysis; and for mammary implants.

The process of soft tissue augmentation is said to occur by injecting or implanting the ceramic material matrix into the chosen tissue at the desired augmentation site and forming a bleb or blister. Subsequently, autogenous tissue growth into the matrix will occur and will closely resemble the endogenous surrounding tissue in texture and properties.

U.S. Pat. No. 5,752,974 (Hereinafter the '974 Patent)

The '974 patent discloses implantable biomaterials and methods for completely blocking, augmenting, sealing, or filling various biological lumens and voids existing within the body of a patient. A range of varying biomaterials compositions and techniques are presented for this purpose.

The described biomaterials should be capable of persisting at the site of placement for at least six (6) months time, and preferably will endure for two (2) calendar years or longer. The preferred biomaterials include (alone or in combination): all naturally occurring or synthetic polymers, especially collagen, fibrin, and elastin in any of their know forms; various synthetic peptides such as (poly)lysine; polysaccharides such as glycosaminoglycans (e.g., hyaluronic acid); diverse proteoglycans; and various polymeric hydrogels.

The biomaterial can also take alternative formats in its preparation. These include: a composition comprising a biomaterial and a cross-linking agent before substantial cross-linking has occurred; a composition comprising a dehydrated cross-linked biomaterial and a non-aqueous carrier; and a dehydrated composition formed of cross-linked biomaterial. All of the disclosed formulations are conventionally known and previously described in the patent and/or scientific literature.

The mode of activity in-vivo for all the disclosed biomaterial compositions is solely and exclusively via direct action. Thus, after implantation, the biomaterial composition itself must create a tight seal or strong adhesion with the patient's own tissues and organs. Such direct adhesion and physical anchorage to the internal tissues and organs in-vivo is said to prevent leakage and to allow complete blockage of the existing opening or void space that is needed to be blocked or filled. Accordingly, it is only after the void or opening has been physically sealed or blocked by the implanted biomaterial that the host tissues expected subsequently to provide an ingrowth of cells, an event which over time is said to strengthen further the adhesion of the anchored biomaterial already previously introduced into the living tissues.

U.S. Pat. No. 5,523,291 (Hereinafter the '291 Patent)

The '291 patent is directed to injectable compositions for soft tissue augmentation, especially breast augmentation. The particular problem addressed and corrected by the '291 patent is the use of cross-linked collagen fibers for breast augmentation, which are unfortunately resorbed in-vivo within a very short time after implantation.

The '291 patent discloses an injectable implant composition for soft tissue augmentation, which comprises elastin and collagen in admixture with a biocompatible carrier; and wherein the fibrous material has been comminuted to break up the natural collagen and elastin matrix.

Moreover, the '291 patent also describes a number of uses for the chemically treated collagen/elastin injectable compositions. Their primary uses, as stated, are for breast augmentation. However, other proposed uses include application as a dermal implant to remove wrinkles, primarily around the face and neck; overcoming urinary incontinence by injection into the urethral sphincter; augmentation of load-bearing tissue, such as under a corn; and as facial contour corrections for the nose, for pock-marks, and for acne scars.

Accordingly, despite all these developments to date, there remains a recognized and continuing need for further improvements in alternative procedures which are minimally invasive and which provide effective clinical treatment methods for the closure of hernias and other naturally occurring lumens and void spaces found in the human body. All such improvements in such alternative medical procedures and techniques would be readily seen as a major contribution and outstanding benefit in this medical field.

SUMMARY OF THE INVENTION

The present invention has multiple aspects.

A first aspect provides a minimally invasive clinical method for closing the spatial void of an umbilical hernia in a living subject, said method comprising the steps of:

obtaining a prepared polysaccharide gel composition comprised of dextran particles and hyaluronic acid and in which there is an absence of preformed fibers;

percutaneously introducing a predetermined quantity of said prepared polysaccharide gel composition to the anatomic locale of the umbilical hernia;

allowing said introduced polysaccharide gel composition to induce an ingrowth of fibroblasts at the anatomic locale of the umbilical hernia; and permitting said ingrowth of fibroblasts to generate newly formed collagen fibers in-situ at the anatomic locale of the umbilical hernia, whereby the spatial void of the umbilical hernia becomes substantially closed.

A second aspect of the invention presents a minimally invasive clinical method for closing the spatial void of a hernia in a living subject, said method comprising the steps of:

anatomically identifying the locale of the spatial void of the hernia in the living subject;

obtaining a prepared polysaccharide gel composition comprised of dextran particles and hyaluronic acid and in which there is an absence of preformed fibers;

percutaneously introducing a predetermined quantity of said prepared polysaccharide gel composition to the anatomic locale of the hernia;

allowing said introduced polysaccharide gel composition to induce an ingrowth of fibroblasts at the anatomic locale of the hernia; and permitting said ingrowth of fibroblasts to generate newly formed collagen fibers in-situ at the anatomic locale of the hernia, whereby the spatial void of the hernia becomes substantially closed.

A third aspect of the invention offers a minimally invasive clinical method for closing the spatial void of an abnormal opening in a living subject, said method comprising the steps of:

anatomically identifying the locale of the abnormal opening in the living subject;

obtaining a prepared polysaccharide gel composition comprised of dextran particles and hyaluronic acid and in which there is an absence of preformed fibers;

percutaneously introducing a predetermined quantity of said prepared polysaccharide gel composition to the anatomic locale of the abnormal opening;

allowing said introduced polysaccharide gel composition to induce an ingrowth of fibroblasts at the anatomic locale of the abnormal opening; and permitting said ingrowth of fibroblasts to generate newly formed collagen fibers in-situ at the anatomic locale of the abnormal opening, whereby the spatial void of the abnormal opening becomes substantially closed.

BRIEF DESCRIPTION OF THE FIGURES

The present invention may be more easily understood and better appreciated when taken in conjunction with the accompanying Drawing, in which.

DETAILED DESCRIPTION OF THE PRESENT INVENTION

The subject matter as a whole comprising the present invention is an entirely unique and unforeseen medical treatment method and alternative to conventional surgery operations and routine surgical techniques. The applications can be used for the in-vivo closure of lumens and voids which naturally occur and exist internally within the soft connective tissue and organs of the living human body; can be employed to advantage for the closure of hernias generally; and is centered upon the closure of umbilical hernias specifically.

I. The Minimally Invasive Clinical Methodology

The Steps of the Clinical Treatment Procedure:

The present invention is a new percutaneous closure method which is expected to be employed under reasonable and realistic clinical treatment conditions. The closure methodology therefore preferably follows a proper clinical routine, which typically includes the following acts:

As a preliminary matter, the physician or surgeon should place the living patient under light anesthesia, for the patients own comfort and safety. The choice of anesthesia is conventional and to be decided by the physician or surgeon in accordance with standard medical practices and with proper regard for the individual needs and personal tolerances and intolerances of the patient undergoing treatment.

The anatomic site and locale of the abnormal opening or hole in the body of the patient has been well established and can be both found and accessed percutaneously in the patient on-demand. Normal examination and radiological test procedures are presumed to have been conducted prior to the day of clinical treatment.

Using a small bore needle, a prepared polysaccharide gel composition which comprises dextranomer microspheres and hyaluronic acid is injected percutaneously through the skin of the patient and into the appropriate anatomic site where an abnormal opening, lumen or void has been found to exist in the patient. The amount or quantity of prepared polysaccharide gel composition should be sufficient to cover the naturally occurring hole then existing internally within the connective tissues of the patient.

Once in proper anatomic site position, the polysaccharide gel composition introduced into the abnormal opening, lumen or void is pharmacologically active and is able to induce an ingrowth of fibroblasts in-situ at the chosen anatomic site. The primary result and direct event caused by the introduced polysaccharide gel composition is thus solely the induction of new fibroblasts in-situ.

After a short time period, and as a subsequently occurring event and secondary consequence, the induced ingrowth of fibroblasts in-situ acts as a causative agent and functions as living cells able to generate newly formed collagen fibers in-situ around the dextranomer microspheres of the introduced gel composition. This secondary generation of fibrous matter in-situ creates the physical mass by which the abnormal opening becomes permanently closed and sealed.

The Method's Singular Aspects and Unforeseen Advantages:

1. The clinical treatment procedure can be used for the closure of umbilical hernias; and for the closure of other types of hernias commonly encountered as medical abnormalities; and for the closure of holes, lumens and void spaces generally which are considered to be abnormal, naturally occurring, and exist internally within the human body.

2. Any conventionally known medical apparatus or device having a penetrating hollow needle as a component part can be employed for delivery of the prepared polysaccharide gel composition. Thus, a conventionally known needle syringe, or an intravenous infusion apparatus, or any automated medical device having a small bore needle which can be placed against the skin of the patient at a pre-chosen location and employed to infuse or inject a gel composition percutaneously can be utilized.

3. There are no pre-existing collagen or elastin fibers at all in the formulation or chemical composition of the prepared polysaccharide gel composition which is employed in the present closure method. To the contrary, there is a complete absence of either collagen, elastic, or any other fiber in any form, cross-linked or not cross-linked, within the polysaccharide gel formulation and composition itself.

4. Once introduced into the spatial volume of the hole, opening, lumen or void space existing internally within the tissues of the patient, the polysaccharide gel composition does not function in-vivo as a direct blocking mass or sealing agent; and the introduced gel composition is never utilized in-vivo either as a solid filler matrix or as a hole plugging material.

Instead, the empirically demonstrated in-vivo effect and consequence of introducing a prepared polysaccharide gel into the spatial volume of a hole, lumen or void is that the dextranomer microspheres of the gel induce a new ingrowth of fibroblasts at the site of its introduction; and that the new ingrowth of fibroblasts, as a secondary consequence, in turn generate newly generated collagen fibers in-situ around the dextranomer microspheres. This indirect formation and aggregation of newly formed collagen/elastin fibers as a discrete mass at the anatomic site then serves to occlude and fill the spatial volume of the defect opening which previously existed at that anatomic location.

5. The present closure methodology provides only an indirect mode of biological activity in-situ. The introduced gel composition directly acts only to induce new fibroblasts growth at the site of the abnormality, but does not itself provide or form the fibrous matter which is subsequently generated in-situ and can be later found at the site of the closed hole. This difference and distinction as to in-vivo mode of activity for the prepared polysaccharide gel composition provides and creates the minimally invasive technique and mechanism of action for a prompt and effective closure of hernias in-vivo.

II. The Prepared Polysaccharide Gel Compositions

It will be noted and appreciated that the present invention is a clinical treatment methodology; and is a treatment procedure which is expected and intended to employ a wide and diverse range of conventionally known and well recognized polysaccharide gel compositions as a prepared-in-advance formulation. Clearly therefore, the methodology has not itself created, or generated, or formulated any novel chemical compositions as such. To the contrary, the present invention relies solely upon previously known chemical formulations and employs only conventionally available preparations of such polysaccharide gels as a prepared chemical composition.

Overall therefore, there are only two critical requirements for the prepared polysaccharide gel compositions to be deemed as suitable and useful in the present closure methodology. These are:

(a) The gel preparation is a stable composition comprising not less than two well known kinds of polysaccharides, dextran particles and hyaluronic acid; and (b) The gel preparation is effectively devoid of any discrete fibers or preformed fibrous matter generally, and there is an absence of any formed collagen and/or elastin fibrous matter within the formulation.

Concerning the first requirement, the two types of polysaccharides can be prepared and be present in any conventionally known shape, size, or concentration; but it is preferred that a mixture of dextranomer microspheres and a stabilized form of hyaluronic acid be employed together, as described in detail within U.S. Pat. No. 5,827,937. As disclosed therein, a wide and diverse range of cross-linked biocompatible polysaccharide gel compositions comprising dextran particles and hyaluronic acid can be prepared. As long as both of the essential requirements listed above are met by the individual formulation, any and all of these are deemed to be suitable for use in the present treatment methodology.

Moreover, a number of additional methods for preparing other suitable polysaccharide gel composition are commonly available. These are represented and illustrated by the disclosures of: Laurent et al., *Acta Chem Scand* 18: 274 (1964); EPO Publications Nos. 0-161-887B1 and 0-265-116A2; and U.S. Pat. Nos. 4,716,154; 5,128,326; and 5,399,351. The text of each of these individual publications is expressly incorporated by reference herein.

Nevertheless, the most preferred formulation of the prepared cross-linked polysaccharide gel suitable for use in the methodology of the present invention is presently manufactured and commercially sold by Q-Med Corporation (Sweden); and is FDA approved and sold under the mark DEFLUX. A host of technical literature is provided by Q-Med Corporation which describes the DEFLUX polysaccharide gel composition in marked detail. In addition, any and all chemical substitutions and variants from the DEFLUX formulation are deemed to be conventionally known and routine matters easy performed by any person ordinarily skilled in the chemical/pharmaceutical arts.

III. The Scope Of The Intended Clinical Applications

The present invention has multiple uses and clinical application. It is a method for a minimally invasive corrective treatment of a hole, lumen, or void space in the living body—but is a technique which is applicable to diverse medical purposes and can be effectively employed at many different anatomic site locales. In its broadest context, the invention is a percutaneous method for the in-vivo closure of an abnormal internal opening which is naturally occurring and pre-existing within the body of a living human or animal subject. In this respect, only the intended anatomic location and/or specific type or kind of abnormal opening to be closed and sealed via this percutaneous treatment process need be identified.

Accordingly, a very specific use for the percutaneous treatment method is for the closure of umbilical hernias. This instance is merely one example of a particular medical usage.

A second category of intended therapeutic treatments and clinical applications encompasses the other medically known types of hernias. These medical treatments are for the closure of diaphragmatic, epigastric, esophageal, hiatal, incarcerated, inguinal, peritoneal, retrosternal, Richter's, and strangulated hernias. Each of these is anatomically unique and is routinely considered a different clinical problem.

A third category of intended clinical applications includes any and all anatomically sited lumens, voids, and cavities—so long as these anatomic spatial volumes are abnormal openings, and are previously internally in existence within the body, and are naturally occurring in the living subject.

IV. Clinical Histories, Empirical Data, and Results

To demonstrate the merits and value of the present invention, a series of planned clinical treatments and empirical data are presented below. It will be expressly understood, however, that the clinical treatments and results described herein and provided below are merely the best evidence of the subject matter as a whole which is the present invention; and that the presented information, while limited in content, is merely illustrative of the present invention as envisioned and claimed.

Illustrative recitations and representative examples of the preferred manner and mode for practicing the methodology are also presented below for the reader's benefit. It will be expressly understood, however, that the recited steps and manipulations presented below are subject to typical variances and changes in the procedural details; all of which are deemed to be customary and routine in the medical field, and may be altered at will to accommodate the needs or conveniences of the practitioner. Accordingly, the specifics of the clinical applications recited herein do not limit nor restrict the intended scope of the present invention in any degree, manner, or detail.

A. An Exemplary Clinical Case History

The Patient

Figure 1:
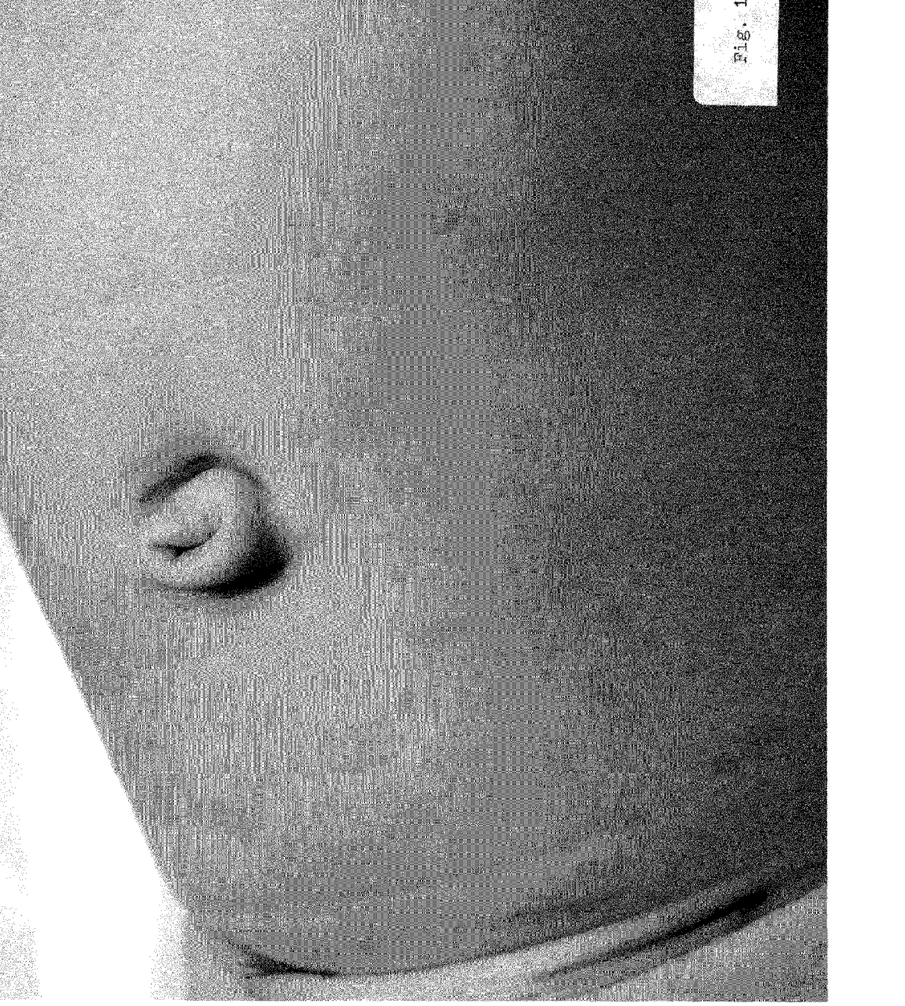
FIG. 1 is an image showing a child with bilateral inguinal hernias and an umbilical hernia.

The patient was a male infant of 6 months age and determined to be in reasonable nutritious health. The pre-operative diagnosis was that the infant suffered a right inguinal hernia; and there was a serious question of whether or not there was a left inguinal hernia as well. An image of a child with bilateral inguinal hernias and an umbilical hernia is provided by FIG. 1.

On this diagnostic basis, the recommended surgical procedure was a bilateral inguinal hernia repair, as well as a closure of the umbilical hernia via a percutaneous injection of DEFLUX polysaccharide gel composition.

Parental Consent

Prior to the date of surgery, express knowing consent for using and injecting DEFLUX polysaccharide gel composition for the closure of the umbilical hernia was discussed and obtained from the parents of the infant patient. The parents have true knowledge and awareness of the attendant risks and benefits for the new minimally invasive closure procedure; and a special consent agreement was prepared and signed by the parents for the treatment of the infant's umbilical hernia with DEFLUX polysaccharide gel.

The Surgical Procedure

Under successful general anesthesia used for surgical repair of inguinal hernia, the patient was prepped and draped in accordance with standard medical practices. A typical surgical repair of a bilateral inguinal hernia was then performed in a conventional manner. After this surgical repair had been successfully completed, the new procedure for repairing the umbilical hernia was initiated.

The Percutaneous Treatment Method

With a finger placed into the defect (the spatial void), 1 cc of DEFLUX polysaccharide gel was injected at four different orientation positions: at the 12:00 o'clock position; at the 3:00 o'clock position; at the 6:00 o'clock position; and at the 9:00 o'clock position. The four injections were performed and completed without difficulty using a sterile syringe having a 25 gauge needle tip.

Figure 2:
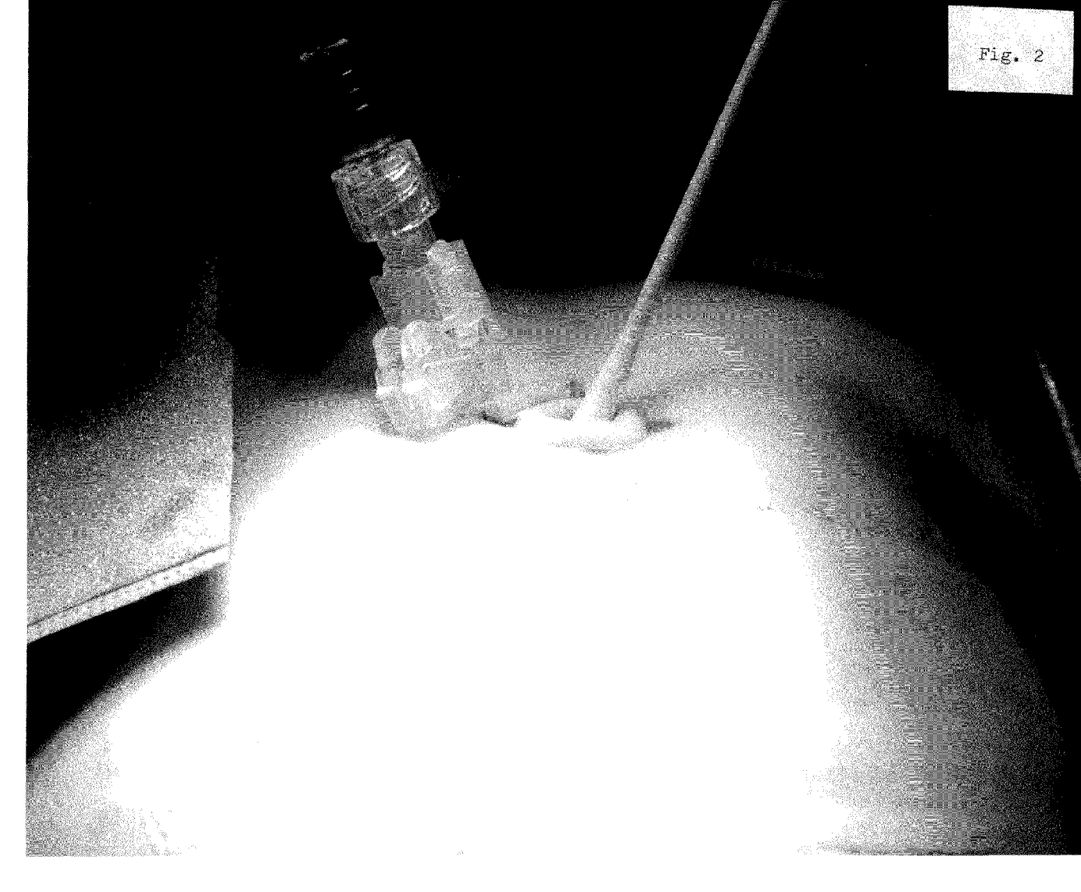
FIG. 2 is an image showing the injection of DEFLUX polysaccharide gel into the four quadrants of the rim of the umbilical defect.

An image of the injection of DEFLUX polysaccharide gel into the four quadrants of the rim of the umbilical defect is shown by FIG. 2. The Q-tip seen in FIG. 2 is merely an aid to finding the edge of the linea alba of the midline and the inner border of the rectus muscle.

After the injections of DEFLUX polysaccharide gel were made in this manner, the spatial void in the umbilicus—which was originally about 1.5 cm in size—then appeared to be smaller than 0.5 cm in size.

Also, following these injections of DEFLUX polysaccharide gel, the umbilicus then appeared to be in excellent condition; and was seen to have tolerated the gel injection procedure quite well. A roll of gauze was placed on the umbilicus as a protective covering; and a Tegaderm dressing was placed over the gauze roll for a minimal type of pressure dressing.

Post-Operative Status

Post-operatively, both the inguinal wound and the umbilical wound were dry to the touch. The patient awoke; the anesthesia appeared to be well tolerated; and the patient was in excellent condition when moved into the recovery room.

The post-operative vital signs were stable and the patient was afebrile. The infant was taking a per oral diet; and it was felt that, upon discharge, the infant could take Tylenol liquid by mouth as the followup medical regimen.

Clinical Result

Figure 3:
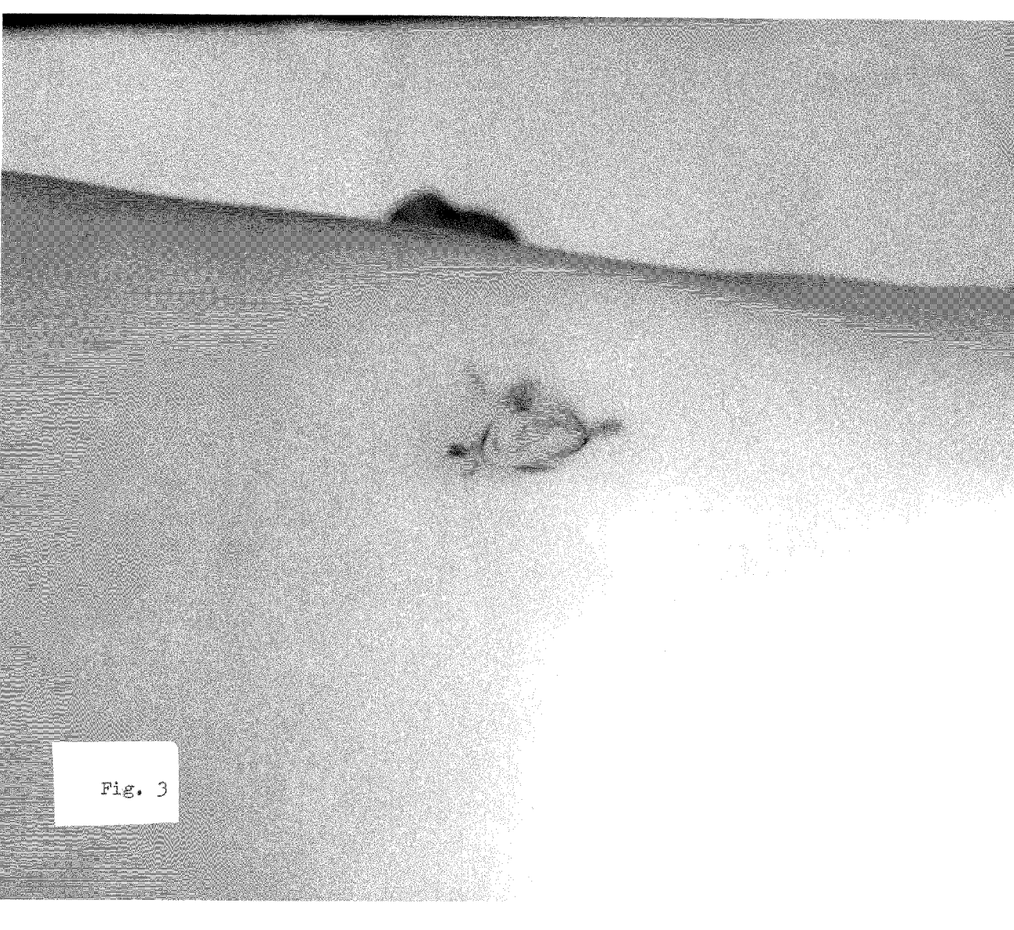
FIG. 3 is an image showing an early postoperative condition wherein the spatial void of the umbilical hernia defect has been closed.

The patient was examined one week post-operatively. An image of the early postoperative stage is shown by FIG. 3. The umbilical hernia, which originally measured 1.5 cm in this patient, was found to be about 80% closed. It was expected that ingrowth stimulation in-situ and subsequent fibrotic activity in-vivo would continue and serve to complete the closure process over a very short time period.

B. A Followup Clinical Study

Study Parameters

A clinical study was conducted which successfully injected DEFLUX polysaccharide gel for correction of umbilical hernias. In this clinical trial, nine patients were percutaneously injected with 2 cc to 5 cc of DEFLUX gel, depending on the clinical volume size of the hernia. No adverse effects of the injection have been noted in any of the nine patients.

The sizes of the hernias have individually ranged from 4 mm to 12 mm. Four of the patients had another surgical procedure performed while under the same anesthesia. These other surgical procedures were inguinal hernia repair; hypospadias repair; and circumcision revision. The other five patients had the minimally invasive closure of their umbilical hernias done as a solo procedure. The details for each patient injected with DEFLUX gel for umbilical hernia closure is presented by Table E1 below.

TABLE E1

Patients Injected With DEFLUX Gel

| Patient/Hernia Size | Date of Birth | Date of Injection/Amount | 1$^{st}$ follow-up visit | 2$^{nd}$ visit | Result | Complications |
|---|---|---|---|---|---|---|
| DSR 1 cm defect | Nov. 29, 2004 | Mar. 10, 2005 4 cc | Apr. 5, 2005 small opening | May 15, 2005 pinpoint opening | Phone Mar. 7, 2006 Mom says hernia gone/no sign of hernia | None |
| TW 4 mm defect | Jun. 27, 2000 | Oct. 27, 2005 2.5 cc | Nov. 1, 2005 no sign of hernia | | Phone Mar. 7, 2006 no sign of hernia/no palpable hernia | None |
| NH 5 mm defect | Apr. 1, 2005 | Dec. 8, 2005 2 cc | Dec. 27, 2005 no sign of hernia | Feb. 7, 2006 small opening | | None |
| HM 5 mm defect | Sep. 22, 2004 | Dec. 16, 2005 2 cc | Mar. 14, 2006 no sign of hernia | | No hernia | None |
| CD 4 mm defect | Jul. 10, 2005 | Dec. 16, 2005 2 cc | Mar. 14, 2006 no sign of hernia | | No hernia | None |
| NC 4 mm defect | Nov. 5, 2004 | Jan. 12, 2006 2 cc | Jan. 17, 2006 hernia present | | | None |
| JP 4 mm defect | Oct. 8, 1999 | Jan. 12, 2006 2 cc | Jan. 17, 2006 no sign of hernia | | No hernia | None |
| AC 8 mm defect | Jun. 1, 1996 | Feb. 10, 2006 4.5 cc | Feb. 28, 2006 no sign of hernia | | No hernia | None |
| AP Over 1 cm defect | May 20, 1996 | Feb. 23, 2006 5 cc | Feb. 28, 2006 small remaining defect | | | None |

Clinical Results

All of the patients treated with DEFLUX gel have markedly improved. All measured hernias are now either closed or are smaller in size than the preoperative defect. No side effects or complications have been identified. Six umbilical hernias have become completely closed and sealed after the injection of DEFLUX gel, with no residual void space being detected. These six patients have been followed in time from one month to a year post-operatively.

It is also noteworthy, as well as interesting, that one patient had a residual defect—some detected void space—at three months time post-operatively that was no longer present at one year's time post-operatively. By this evidence, it is believed that the natural propensity of umbilical hernias to close can be enhanced and assisted by the injection of DEFLUX gel; In this manner, if some residual defect (void space) initially remains soon after the injection with DEFLUX gel, the original hernia defect is expected to proceed slowly to final correction and complete closure over a longer course of time.

At this time, six of the original nine hernias are completely closed. Three patients appear to have a residual void space defect, all at less than three months' time following the injection of DEFLUX gel. One of the three patients was found to have had no defect at nineteen days post-operatively, but subsequently was found to have a small sized void defect at the two month follow-up examination.

All the remaining defects are substantially smaller in size than their original, preoperative umbilical hernia size.

The present invention is not to be limited in form nor restricted in scope except b the claims appended hereto.

What I claim is:

1. A minimally invasive clinical method for closing the spatial void of an umbilical hernia in a living subject using a polysaccharide delivery device, said method comprising the steps of:

obtaining a prepared-in-advance polysaccharide gel composition consisting essentially of dextran particles and hyaluronic acid as the active ingredients and in which there is a complete absence of preformed collagen and elastin fibers;

percutaneously introducing, by the polysaccharide delivery device, a predetermined quantity of said prepared in-advance polysaccharide gel composition to the anatomic locale of the umbilical hernia;

inducing an ingrowth of fibroblasts at the anatomic locale of the umbilical hernia using said introduced polysaccharide gel composition;

generating newly formed fibers in-situ at the anatomic locale of the umbilical hernia using said ingrowth of fibroblasts;

forming and aggregating said newly formed fibers in-situ; and occluding and filling said spatial void to substantially close the umbilical hernia by said newly formed fibers generated in-situ at the anatomic locale of the umbilical hernia.

2. A minimally invasive clinical method for closing the spatial void of a hernia in a living subject using a polysaccharide delivery device, said method comprising the steps of:

anatomically identifying the locale of the spatial void of the hernia in the living subject;

obtaining a prepared in-advance polysaccharide gel composition consisting essentially of dextran particles and hyaluronic acid as the active ingredients and in which there is a complete absence of preformed collagen and elastin fibers;

percutaneously introducing, by the polysaccharide delivery device, a predetermined quantity of said prepared in-advance polysaccharide gel composition to the anatomic locale of the hernia;

inducing an ingrowth of fibroblasts at the anatomic locale of the hernia using the introduced polysaccharide gel composition;

generating newly formed fibers in-situ at the anatomic locale of the hernia using the ingrowth of fibroblasts;

forming and aggregating the newly formed fibers in-situ; and occluding and filling the spatial void to substantially close the hernia by said newly formed fibers generated in-situ at the anatomic locale of the umbilical hernia.

3. The clinical method as recited in claim 1 or 2 wherein said prepared in-advance polysaccharide gel composition further comprises dextranomer microspheres and hyaluronic acid.

4. The clinical method as recited in claim 1 or 2 wherein said prepared-in-advance polysaccharide gel composition is a cross-linked polysaccharide gel composition including dextranomer microspheres and hyaluronic acid.

5. The clinical method as recited in claim 1 or 2 wherein said percutaneous introduction by the polysaccharide delivery device is made using a small bore needle tip.

6. The clinical method as recited in claim 2 wherein said hernia is selected from the group consisting of diaphragmatic, epigastric, esophageal, hiatal, incarcerated, inguinal, peritoneal, retrosternal, Richter's, and strangulated hernias.

7. The clinical method as recited in claim 1 or 2 wherein said newly generated fibers formed in-situ are collagen fibers.

8. The clinical method as recited in claim 1 or 2 wherein said newly generated fibers formed in-situ are elastin fibers.

* * * * *

UNITED STATES PATENT AND TRADEMARK OFFICE
CERTIFICATE OF CORRECTION

PATENT NO. : 7,655,639 B2  Page 1 of 1
APPLICATION NO. : 11/386882
DATED : February 2, 2010
INVENTOR(S) : Neil R. Feins It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 479 days.

Signed and Sealed this

Twenty-third Day of November, 2010

David J. Kappos
*Director of the United States Patent and Trademark Office*